United States Patent
Nakano et al.

(10) Patent No.: US 10,717,963 B2
(45) Date of Patent: Jul. 21, 2020

(54) METHOD FOR CULTURING LACTIC ACID BACTERIA, AND A FOOD AND DRINK PRODUCT

(75) Inventors: Masatoshi Nakano, Minato-ku (JP); Mika Arifuku, Minato-ku (JP); Harumi Mizukoshi, Minato-ku (JP); Susumu Mizusawa, Minato-ku (JP); Kazumasa Kimura, Minato-ku (JP); Masahiko Ito, Minato-ku (JP)

(73) Assignee: KABUSHIKI KAISHA YAKULT HONSHA, Minato-ku, Tokyo (JP)

( * ) Notice: Subject to any disclaimer, the term of this patent is extended or adjusted under 35 U.S.C. 154(b) by 0 days.

(21) Appl. No.: 13/260,772

(22) PCT Filed: Mar. 19, 2010

(86) PCT No.: PCT/JP2010/054826
§ 371 (c)(1),
(2), (4) Date: Sep. 28, 2011

(87) PCT Pub. No.: WO2010/113680
PCT Pub. Date: Oct. 7, 2010

(65) Prior Publication Data
US 2012/0040054 A1   Feb. 16, 2012

(30) Foreign Application Priority Data

Mar. 31, 2009   (JP) .................. 2009-086305

(51) Int. Cl.
A23C 9/123      (2006.01)
C12N 1/20       (2006.01)
C12N 1/04       (2006.01)

(52) U.S. Cl.
CPC .............. *C12N 1/20* (2013.01); *A23C 9/1234* (2013.01); *C12N 1/04* (2013.01); *A23Y 2220/17* (2013.01)

(58) Field of Classification Search
USPC .................................................. 426/43, 580
See application file for complete search history.

(56) References Cited

U.S. PATENT DOCUMENTS

| | | | |
|---|---|---|---|
| 4,053,642 A * | 10/1977 | Hup et al. ................ | 426/36 |
| 4,178,390 A * | 12/1979 | Igoe ........................ | A23C 9/137 |
| | | | 426/43 |
| 4,374,155 A * | 2/1983 | Igoe ........................ | A23C 9/1315 |
| | | | 426/564 |
| 4,376,791 A * | 3/1983 | Holbrook et al. ........ | 426/565 |
| 4,544,636 A * | 10/1985 | Bily ........................ | 435/252.9 |
| 4,692,338 A * | 9/1987 | Irvine et al. ............. | 426/2 |
| 4,748,026 A * | 5/1988 | Keefer .................... | A23C 9/137 |
| | | | 426/43 |
| 4,968,513 A * | 11/1990 | Watanabe et al. ........ | 426/42 |
| 6,759,067 B1 * | 7/2004 | Ogasawara et al. ..... | 426/34 |
| 2006/0240149 A1 * | 10/2006 | Konkoly et al. ........ | 426/34 |

FOREIGN PATENT DOCUMENTS

| | | |
|---|---|---|
| EP | 0937407 A1 | 8/1999 |
| JP | 62-91143 | 4/1987 |
| JP | 8-116872 | 5/1996 |
| JP | 2005-130804 | 5/2005 |

OTHER PUBLICATIONS

Joint FAO WHO Expert Committee on Food Additives 1965 www.inchem.org/documents/jecfa/jecmono/v38aje10.htm 4 pages.*
A. Gautier "Diet and Dietetics" 1906 Constable and Company LTD pp. 174 and 175.*
Murakami JP 2001-095484 Japanes Machine Translation 2001 4 pages.*
JP 2005-130804 May 26, 2005 AIPN Translation 6 pages.*
International Search Report, Form PCT/ISA/210.
Supplementary European Search Report for International Application EP 10 75 8454, dated May 8, 2013.
Sung-Han Kim et al: "Optimization of Growth and Storage Conditions for Lactic Acid Bacteria in Yogurt and Frozen Yogurt", J. Korean Soc. Appl. Biol. Chem. 52(1), Feb. 1, 2009, pp. 76-79.
"Final Action" dated Jan. 19, 2015 in Taiwanese Patent Application No. 099108617 filed Mar. 24, 2010, which is the Taiwanese counterpart of the present US application.

* cited by examiner

*Primary Examiner* — Felicia C Turner
(74) *Attorney, Agent, or Firm* — Warner Norcross + Judd LLP

(57) ABSTRACT

The object of the present invention is to provide a method of culturing lactic acid bacteria to obtain a lactic acid bacteria culture in which the number of lactic acid bacteria can be stably maintained, and to obtain food and drink products comprising a lactic acid bacteria culture excellent in product stability.

In order to accomplish the object, the present invention provides a method of culturing lactic acid bacteria comprising inoculating lactic acid bacteria to a medium comprising a milk ingredient having a free phosphoric acid concentration of less than 0.25 wt %, and a phosphate, and food and drink products comprising the lactic acid bacteria culture obtained by this culturing method.

6 Claims, No Drawings

METHOD FOR CULTURING LACTIC ACID BACTERIA, AND A FOOD AND DRINK PRODUCT

TECHNICAL FIELD

The present invention relates to a method for culturing lactic acid bacteria, and a food and drink product comprising a lactic acid bacteria culture obtained by the method.

BACKGROUND ART

It is well-known that lactic acid bacteria is used for the production of milk products such as cheese, fermented milk, lactic acid bacteria beverages and the like, and various fermented foods such as Korean Kimchee, pickles and the like. In recent years, various physiological functions of lactic acid bacteria such as intestinal regulation effects and the like have been elucidated, and the fungus body per se of lactic acid bacteria and various lactic acid bacteria cultures are used as materials for health foods and pharmaceutical products, and they are applied to a variety of uses.

Although the culturing of lactic acid bacteria is performed in various forms, the most frequently performed is for the production of lactic acid bacteria formulations, the production of various fermented dairy foods such as fermented milk, lactic acid bacteria beverages, cheese and the like by using a milk ingredient such as animal milk as a medium. However, as the auxotrophy of most of lactic acid bacteria is generally strict, there are many types of lactic acid bacteria that do not sufficiently grow using only a milk ingredient as a medium. In addition, if a certain type of bacteria having a relatively good growth property is used, culturing for a long period of time is necessary to obtain a culture having sufficient acidity (the amount of acid formed) in the production of lactic acid bacteria beverages and the like.

However, culturing of lactic acid bacteria for a long period of time results in a decreased number of living bacteria, and thus there is a problem in the production of lactic acid bacteria beverages and the like in which the number of living bacteria is considered to be important. Therefore, various growth promoting substances capable of increasing the growth of the bacteria to a medium during culturing of lactic acid bacteria are generally added, in order to reduce the culture time. *Chlorella* extract, iron salts, vitamins, protein degradation products comprising amino acids and peptides, yeast extract and the like are known as growth promoting substances or substances confirmed to be effective for increasing growth.

Further, a method using a water extract of Sake lees and/or a water extract of Sake lees which has been treated with a protein degradation enzyme (Patent Publication 1), a method using an extract of the leaves of a Coffee plant (Patent Publication 2), a method using a complex of a fat with a protein (Patent Publication 3) and the like have been. The applicant of the present application found that extracts of tea, green onions and ginger obtained by extraction with an acid are effective as agents for increasing the growth of lactic acid bacteria, and reported the matter (Patent Publication 4).

On the other hand, it is important that living lactic acid bacteria are delivered into the intestines so as to increase various physiological functions by the lactic acid bacteria. Therefore, in order to maintain a high viability of lactic acid bacteria in a culture or a product comprising the same, a method using a composition comprising 20 to 90 wt % of a fat in which phospholipids account for 40 to 55 wt %, with respect to all solid components (Patent Publication 5), and a method using dead fungus bodies of lactic acid bacteria (Patent Publication 6) were proposed.

PRIOR ART REFERENCES

[Patent Publication 1] Japanese Patent Laid-open No. 5-15366
[Patent Publication 2] Japanese Patent Laid-open No. 6-125771
[Patent Publication 3] Japanese Patent Laid-open No. 2006-230259
[Patent Publication 4] Patent publication No. 3648115
[Patent Publication 5] Japanese Patent Laid-open No. 2007-97447
[Patent Publication 6] Japanese Patent Laid-open No. 2008-5811

SUMMARY OF THE INVENTION

Problems to be Solved by the Invention

However, the quality of milk ingredients, a natural product, is not constant, as it depends on the season, production area, processing method and the like. Therefore, even when known materials that were confirmed to be effective for increasing the growth properties and viability of lactic acid bacteria were used in a medium comprising the milk ingredient as a material during culture of lactic acid bacteria, for example, the number of lactic acid bacteria in the resulting culture caused not to be maintained constant, and when this culture was used for the production of food and drink products or the like, the number of living bacteria showed precipitous drops after preservation of the food and drink products or the like.

Accordingly, the object of the present invention is to provide a method for culturing lactic acid bacteria so as to obtain a lactic acid bacteria culture in which the number of the lactic acid bacteria can be stably maintained.

Further, the object of the present invention is to obtain a food and drink product comprising a lactic acid bacteria culture having excellent product stability.

Means for Solving the Problems

The inventors of the present application keenly studied to solve the above problems, and as a result, found the technical findings that the quality of a milk ingredient used in a medium affects the stabilization of the number of lactic acid bacteria in lactic acid bacteria fermented products, and in particular, confirmed that a lactic acid bacteria culture in which the number of lactic acid bacteria can be stably maintained cannot be obtained using a medium comprising a milk ingredient having a free phosphoric acid concentration of less than 0.25 wt %. In addition, the inventors of the present application found that when a milk ingredient is used as a medium, stabilization of the number of lactic acid bacteria in the obtained lactic acid bacteria fermented products is increased by adding a phosphate to the medium, to complete the present invention.

Further, the inventors of the present application found that food and drink products such as fermented milk products and the like having excellent product stability can be produced using this culture.

Namely, the present invention provides a method for culturing lactic acid bacteria comprising inoculating lactic acid bacteria to a medium comprising a milk ingredient having a free phosphoric acid concentration of less than 0.25 wt % and a phosphate.

In addition, the present invention provides a method for culturing lactic acid bacteria comprising inoculating lactic acid bacteria to a medium comprising a milk ingredient having a free phosphoric acid concentration of less than 0.25 wt, and a protein content per solid nonfat milk component (SNF) of less than 35 wt %, and a water-soluble phosphate. It is preferable that skim milk powder is used as the milk ingredient.

Further, the present invention provides a food and drink product comprising a culture obtained by inoculating lactic acid bacteria to a medium comprising a milk ingredient having a free phosphoric acid concentration of less than 0.25 wt % or a milk ingredient having a free phosphoric acid concentration of less than 0.25 wt %, and a protein content per solid nonfat milk component (SNF) of less than 35 wt %, and a water-soluble phosphate, and, culturing the same.

Effect of the Invention

According to the method of the present invention, if a milk ingredient whose quality varies, depending on the season, production area, processing procedural steps or the like because it is a natural product is used, a lactic acid bacteria culture in which the number of lactic acid bacteria can be stably maintained can be obtained, and the lactic acid bacteria culture can be applied to a wide range of various health foods and pharmaceutical products.

In addition, according to the method of the present invention, as a culture stably comprising a large number of lactic acid bacteria exhibiting high activity can be obtained by combining substances known to be effective to increase the growth property and viability of the lactic acid bacteria, it is especially appropriate for the production of fermented milk food such as lactic acid bacteria beverages and the like in which the number of living bacteria is considered to be important.

Further, according to the method of the present invention, a milk product which is a natural product can be used as a material in a medium for culturing lactic acid bacteria, irrespective of the season, production area, processing procedural steps or the like.

MODE FOR CARRYING OUT THE INVENTION

A milk ingredient having a free phosphoric acid concentration of less than 0.25 wt % is used as the milk ingredient in a medium for culturing lactic acid bacteria in the present invention. The free phosphoric acid concentration of a milk ingredient is determined by a known method such as a method using molybdic acid (the molybdenum blue method) or the like to confirm whether the milk ingredient has a free phosphoric acid concentration within the above range. The term milk ingredient means a material comprising a milk protein herein. Specific examples thereof include animal milk such as cows milk, goats milk and the like, skim milk powder, whole milk powder, fresh cream and the like.

A method for measuring the free phosphoric acid concentration of the milk ingredient will be explained below, using skim milk powder as an example of the milk ingredient. Please note that the value measured by the following method is defined to be the free, phosphoric acid concentration of the milk ingredient in the specification of the present application.

<<Method for Measuring Free Phosphoric Acid Concentration>>
(1) Reagents
 (a) Ascorbic Acid Solution (72 g/L)
 7.2 g of L(+)-ascorbic acid (Wako Pure Chemical Industries, Ltd., Special Grade) is dissolved in water to prepare a solution having a total volume of 100 mL, and the solution is stored in a dark place at a temperature of 0 to 10° C.
 (b) Ammonium Molybdate Solution
 6.0 g of hexaammonium heptamolybdate tetrahydrate (Wako Pure Chemical Industries, Ltd., Special Grade) and 0.24 g of bis[(+)-tartrato]diantimonate (III) potassium trihydrate (Wako Pure Chemical Industries, Ltd., Special Grade) are dissolved in water to prepare a solution having a total volume of about 300 mL, and 120 mL of sulfuric acid (2+1) is added to the solution to prepare a solution having a total volume of 500 mL.
 (c) Ammonium Molybdate-Ascorbic Acid Mixture Solution (Color-Forming Solution)
 The ammonium molybdate solution and the ascorbic acid solution (72 g/L) are mixed such that the volume ratio thereof is 5:1 (prepared at the time of use).
 (d) Standard Concentrated Phosphoric Acid Ion Solution (50 μg $PO_4^{3-}$—P/mL)
 Potassium dihydrogen phosphate (for a pH standard solution) is heated at 105±2° C. for about two hours, and is cooled in a desiccator. 0.2197 g thereof is taken to prepare a solution having a total volume of 1000 mL. The solution is stored in a dark place at a temperature of 0 to 10° C.
 (e) Standard Phosphoric Acid Ion Solution (1 μg $PO_4^{3-}$—P/mL)
 1 ml of the standard concentrated phosphoric acid ion solution (50 μg $PO_4^{3-}$—P/mL) is taken to be filled up in a 50 mL volume measuring flask.
(2) Standard Curve
 (i) Water is poured into test tubes such that each volume thereof is 5.0 mL, 4.75 mL, 4.5 mL, 4.0 mL, 3.0 mL or 0.0 mL.
 (ii) The standard phosphoric acid ion solution (1 μg $PO_4^{3-}$—P/mL) is added to each test tube of (i) in each volume of 0.0 mL, 0.25 mL, 0.5 mL, 1.0 mL, 2.0 mL or 5.0 mL to prepare a solution having a total volume of 5.0 mL.
 (iii) 400 μL of the color-forming solution is added, and the mixture solution let sit still for about 15 minutes.
 (iv) The absorbance at UV 880 nm is measured by a spectrophotometer within 30 minutes.
(3) Measurement Procedural Steps
 (i) After a sample (2.0 g of a skim milk powder) is measured, and dissolved in water (or hot water), the solution is filled up in a 100 ml volume measuring flask. The solution is let sit for one hour or longer.
 (ii) About 6 ml of (i) is measured into VIVA SPIN 6 (5,000 MWCO), and is subjected to ultrafiltration by a centrifuge (7,500 G, 30 minutes, 25° C.).
 (iii) The filtrate of (ii) is accurately measured and is poured into a 100 ml volume measuring flask by a 1 ml whole pipette to be filled up with water.
 (iv) The solution of (iii) is measured, and is poured into a test tube by a 5 ml whole pipette.
 (v) 400 μL of the color-forming solution is added, and the solution is let sit for about 15 minutes.
 (vi) The absorbance at UV880 nm is measured by a spectrophotometer within 30 minutes.
 (vii) The free phosphoric acid amount (μg/Vial) is determined, referring to the standard curve obtained in (2). The ratio of the free phosphoric acid contained in the skim milk powder is determined by the formula below, using the obtained free phosphoric acid amount.

% of free phosphoric acid in the skim milk powder=the free phosphoric acid amount (μg/Vial)×10,000 mL/5 mL×100 g/2 g×1 g/1,000,000 μg

*The analytical method was performed, referring to the analytical method of phosphoric acid ions (molybdenum blue (ascorbic acid reduction) absorption photometry) in the food ingredient test method and JIS K0102 (factory effluent test method, 1998).

In the present invention, a milk ingredient in which the free phosphoric acid concentration determined by the above method is less than 0.25 wt %, and the protein content per solid nonfat milk component (SNF) is less than 35 wt % is exemplified as a preferable milk ingredient used in the medium for culturing lactic acid bacteria.

The protein content per solid nonfat milk component (SNF) can be calculated by Formula 1 below.

$$\frac{\text{protein content in skim milk powder}}{\left(\begin{array}{c}\text{amount of}\\ \text{skim milk}\\ \text{powder (100)}\end{array}\right) - (\text{water content}) - (\text{fat content})} \times 100 \qquad [\text{Formula 1}]$$

The protein content, the fat content and the water content can be calculated, based on the determination methods described in the Standard Table of Food composition in Japan ($5^{th}$ Edition). More specifically, the protein content, the fat content and the water content are determined and calculated by the Kjeldahl method, the Rhese Gotlieb method, and weight loss in the heat-drying method at atmospheric or reduced pressure in the direct method or the drying aid addition method, respectively.

On the other hand, in the present invention, the phosphate used in the medium for culturing lactic acid bacteria with the above milk ingredient includes water-soluble phosphates. More specifically, sodium dihydrogen phosphate, disodium hydrogen phosphate, ammonium dihydrogen phosphate, diammonium hydrogen phosphate, potassium dihydrogen phosphate, dipotassium hydrogen phosphate, trisodium phosphate, tripotassium phosphate and the like are exemplified as preferable examples. It is preferable that two or more of these phosphates are combined to be added to the medium such that the pH of the medium is within the neutral range (pH 6 to 8).

In the present invention, the added amount of the phosphate is set to provide approximately the same concentration as a free phosphoric acid concentration calculated by subtracting the concentration of the free phosphoric acid contained in the milk ingredient from a logical free phosphoric acid concentration of a medium which is assumed to have been prepared using a milk ingredient in which the free phosphoric acid concentration is 0.25 wt % or more, preferably 0.25 wt % to 0.50 wt % as a base material.

Further, the concentration of the milk ingredient in the medium is not especially limited, and is a general concentration. For example, it is 5 to 30 wt %, preferably about 10 to 20 wt %.

Namely, the amount of the phosphate used in the present invention can be determined by the calculation using Formula 2 below. The amount of the phosphate used can be selected as a concentration of the phosphate, presuming all the molecules of phosphoric acid in the phosphate are molecules of free phosphoric acid.

[Formula 2]

$$\frac{\left(\begin{array}{c}\text{free}\\ \text{phosphoric acid}\\ \text{concentration}\\ \text{in base}\\ \text{material}\end{array}\right) - \left(\begin{array}{c}\text{free}\\ \text{phosphoric}\\ \text{acid}\\ \text{concentration}\\ \text{in milk}\\ \text{ingredient}\end{array}\right) \times \left(\begin{array}{c}\text{medium}\\ \text{concen-}\\ \text{tration}\end{array}\right)\left(\begin{array}{c}\text{molecular}\\ \text{weight of}\\ \text{phosphates*}\end{array}\right)}{100 \times \left(\begin{array}{c}\text{molecular weight of}\\ \text{phosphorus}\end{array}\right)}$$

*If two or more kinds of phosphates are used, the average molecular weight thereof is used.

For example, the amount of the phosphates used a mixture of potassium hydrogen phosphate (50%) and potassium dihydrogen phosphate (50%) having an average molecular weight of 155 in a case where a milk ingredient having a free phosphoric acid concentration of 0.20 wt % or 0.24 wt % is used to prepare a medium having a milk ingredient content of 20 wt % can be determined by the calculation below.

(1) When a milk ingredient having a free phosphoric acid concentration of 0.20 wt % is used:

The Lower Limit (0.25−0.20)×20/100×155/31=0.05%

The Upper Limit (0.50−0.20)×20/100×155/31=0.30%

Namely, when a 20 wt % medium is prepared using a milk ingredient having a free phosphoric acid concentration of 0.20 wt %, the phosphates may be added in an amount of 0.05 wt % or more, preferably in an amount ranging from 0.05 to 0.30 wt %. Namely, 0.05 g or more, preferably 0.05 to 0.30 g of the above phosphates may be added to 100 g of the medium comprising 20 wt % of the milk ingredient.

(2) When a milk ingredient having a free phosphoric acid concentration of 0.24 wt % is used:

The Lower Limit (0.25−0.24)×20/100×155/31=0.01%

The Upper Limit (0.50−0.24)×20/100×155/31=0.26%

Namely, when a 20 wt % medium is prepared using a milk ingredient having a free phosphoric acid concentration of 0.24 wt %, the phosphates may be added in an amount of 0.01 wt % or More, preferably in an amount ranging from 0.01 to 0.26 wt %. Namely, 0.01 g or more, preferably 0.01 to 0.26 g of the above phosphates may be added to 100 g of the medium comprising 20 wt % of the milk ingredient.

In the preparation of a medium for culturing lactic acid bacteria in the present invention, if the free phosphoric acid concentration of the medium is lower than the logical free phosphoric acid concentration of the medium which is assumed to have been prepared using a milk ingredient having a free phosphoric acid concentration of 0.25 wt % as a base material, the number of lactic acid bacteria in the obtained lactic acid culture cannot be stably maintained. The number of lactic acid bacteria in food or drink comprising the culture may be decreased, due to the preservation of the food or drink.

On the other hand, if the free phosphoric acid concentration is higher than the logical free phosphoric acid concentration of the medium which is assumed to have been prepared using a milk ingredient having a free phosphoric acid concentration of 0.50 wt % as a base material, stabilization of the number of lactic acid bacteria in the obtained lactic acid bacteria fermented product is increased, but the quality of the food or drink products comprising same may be degraded, due to aggregation or precipitation during preservation of the food or drink products.

In addition, in the present invention, ingredients which are used for general media for lactic acid bacteria, and are other than a milk ingredient having a free phosphoric acid concentration of less than 0.25 wt %, and water-soluble phosphate may be added to the medium used for culturing lactic acid bacteria. Examples of these ingredients include vitamins such as vitamin A, vitamins B, vitamin C, vitamin E and the like, various peptides, amino acids, and salts of calcium, magnesium and the like. The amounts used thereof are not particularly limited.

Lactic acid bacteria are cultured using a medium prepared in the above manner in the present invention. The lactic acid bacteria used in culture are not especially limited so long as they are generally used for the production of food. Examples thereof include *Lactobacillus* genus bacteria such as *Lactobacillus casei, Lactobacillus acidophilus, Lactobacillus cremoris, Lactobacillus helveticus, Lactobacillus salivarius, Lactobacillus gasseri, Lactobacillus fermentum, Lactobacillus yoghurti, Lactobacillus delbrueckii* subsp. *bulgaricus, Lactobacillus delbrueckii* subsp. *delbrueckii, Lactobacillus johnsonii* and the like, *Streptococcus* genus bacteria such as *Streptococcus thermophilus* and the like, *Lactococcus* genus bacteria such as *Lactococcus lactis* subsp. *lactis, Lactococcus lactis* subsp. *cremoris, Lactococcus plantarum, Lactococcus raffinolactis* and the like, and *Enterococcus* genus bacteria such as *Enterococcus faecalis, Enterococcus faecium* and the like.

The culture conditions for these lactic acid bacteria are the most appropriate conditions for general culture of lactic acid bacteria, and are not especially limited. For example, conditions of a temperature of about 30 to 40° C. and about 1 to 7 days are preferable. In addition, as the culture conditions at this time, methods suitable for the culturing of lactic acid bacteria used may be optionally selected from still standing, agitation, shaking, aeration and the like.

The culture obtained by the culture method of the present invention per se or after having been subjected to a sterilization process can be applied to the use as food and drink products, cosmetics, pharmaceutical products and the like. The culture may be used alone, or may be mixed with optional ingredients. In addition, the fungus bodies can be collected from the culture and washed by a means such as centrifugation or the like to be used. Further, the culture method of the present invention can be applied to the production of fungus body enzymes produced by lactic acid bacteria.

When the culture obtained by the culture method of the present invention is used as a drink or food product, the culture may be formulated into fermented milk such as that of plain type, flavored type, fruit type, sweet type, soft type, drink type, solid (hard) type, frozen type or the like, lactic acid bacteria a beverage, kefir, cheese or the like.

In addition, when it is used as a drink or food product, sweeteners such as syrup and the like, and other various food materials, for example, optional ingredients such as various sugars, thickeners, emulsifiers, various vitamin agents and the like may be added as ingredients that may be mixed with the culture. Specific examples of these food materials include sugars such as sucrose, glucose, fructose, palatinose, trehalose, lactose, xylose, maltose and the like, sugar alcohols such as sorbitol, xylitol, erythritol, lactitol, palatinit, reduced glutinous starch syrup, reduced maltose glutinous starch syrup and the like, sweeteners having a high degree of sweetness such as aspartame, thaumatin, sucralose, acesulfame K, stevia and the like, various thickeners (stabilizers) such as agar, gelatin, carrageenan, guar gum, xanthan gum, pectin, locust bean gum, gellan gum, carboxymethylcellulose, soybean polysaccharide, alginic acid propylene glycol and the like, emulsifiers such as sucrose fatty acid esters, glycerin fatty acid esters, polyglycerol fatty acid esters, sorbitan fatty acid esters, lecitin and the like, milk fat such as cream, butter, sour cream and the like, acidulants such as citric acid, lactic acid, acetic acid, malic acid, tartaric acid, gluconic acid and the like, various vitamins such as vitamin A, vitamins B, vitamin C, vitamin E and the like, minerals such as calcium, magnesium, zinc, iron, manganese and the like, flavoring agents of yogurt type, berry type, orange type, quince type, Japanese basil type, citrus type, apple type, mint type, grape type, apricot type, pear type, custard cream, peach, melon, banana, tropical, herb, tea, coffee and the like.

Production of the drink and food product using the culture method of the present invention may be performed by normal techniques, and is not particularly limited. For example, a phosphate is added to a skim milk powder whose free phosphoric acid concentration had been determined to be less than 0.25 wt % in the manner satisfying the predetermined conditions to prepare a medium, the medium is subjected to a sterilization process, lactic acid bacteria are inoculated to the medium, and are cultured, and the medium is subjected to a homogenization treatment to obtain fermented milk. Next, a separately prepared syrup solution is added to the fermented milk, and is mixed. Further, a flavoring agent is added thereto to obtain a final product.

Next, the details of the present invention will be further explained below, with reference to Examples and Test Examples. However, the present invention is not limited by these Examples and the like. Please note that percentage (%) described below is on a weight basis, unless otherwise specified.

EXAMPLES

Test Example 1

(Ingredient analysis of the milk ingredient)

The free phosphoric acid concentration and the protein content of a skim milk powder from Australia manufactured by the Murray Goulburn Corporation (hereinafter only referred to as "Sample") were measured.

(1) Measurement of Free Phosphoric Acid Concentration

The free phosphoric acid concentration of the Sample was measured in accordance with the method described above under the heading "Method for Measuring Free Phosphoric Acid Concentration".

As a result, the free phosphoric acid concentration thereof was 0.23%.

(2) Measurement of Protein Content

The protein content of the Sample was calculated by Formula 1 described above using the following analytical values.

Protein content of the skim milk powder: 32.8%

Water content: 3.8%, Fat content: 0.6%

As a result, the protein content per solid nonfat milk component was 34.3%/SNF.

Example 1

(Preparation of a Lactic Acid Bacteria Culture)

A skim milk powder, phosphates, and glucose were dissolved in water, and the Sample of Test Example 1 was used to prepare a medium having a composition described in Table 1. Please note that the amount of the phosphate used was selected, considering that all the molecules of phosphoric acid in the phosphates are molecules of free phosphoric acid (selected in the same manner, hereinafter). This medium was sterilized at 100° C. for 90 minutes. Next, *Lactobacillus casei* was inoculated such that it accounted for 0.5% of the medium, and was cultured until the pH of the medium became about 3.6, and the pH and the number of lactic acid bacteria of the resulting lactic acid bacteria culture at the end of culture were measured. In addition, 400 mL of liquid sugar syrup of glucose and sucrose, and 1.5 L of sterilized water were added to 600 mL of the culture, and the mixture was homogenized to produce lactic acid bacteria beverages (Products and Comparative Product). The pH and the number of the lactic acid bacteria were measured immediately after the production of the beverages, and after 14 days preservation at 10° C. The results thereof are shown in Table 1 below.

TABLE 1

|  |  | Product | Comparative Product |
|---|---|---|---|
| Medium Composition | Skim milk powder (Sample) | 16% | 16% |
|  | Phosphates* | 0.016% | — |
|  | Glucose | 3% | 3% |
|  | pH after culture | 3.57 | 3.57 |
| Number of living bacteria | After culture | $1.0 \times 10^9$ | $4.1 \times 10^8$ |
|  | Immediately after production of product | $2.2 \times 10^8$ | $9.0 \times 10^7$ |
|  | After 14 day preservation at 10° C. | $1.1 \times 10^8$ | $3.2 \times 10^7$ |

*A mixture of dipottasium hydrogen phosphate (50%) and potassium dihydrogen phosphate (50%)

As is clear from Table 1, it was confirmed that the number of lactic acid bacteria in the lactic acid bacteria beverage produced using the culture obtained by culturing lactic acid bacteria in a medium comprising only the milk ingredient (Sample) having a free phosphoric acid concentration of less than 0.25% as a material was remarkably decreased after the preservation. With respect to this, it was recognized that the number of the lactic acid bacteria in the culture was increased by adding the phosphates to a medium comprising this milk ingredient as a material. Further, an effect to stabilize the number of the lactic acid bacteria was confirmed in the lactic acid bacteria beverage produced using this culture.

Example 2

(Production of Lactic Acid Bacteria Beverages)

A skim milk powder, phosphates, and glucose were dissolved in water, and the Sample of Test Example 1 was used to prepare media having a composition described in Table 2. These media were sterilized at 100° C. for 90 minutes, *Lactobacillus casei* was inoculated such that it accounted for 0.5% of each medium, and was cultured until the pH of the medium became about 3.6 to obtain lactic acid bacteria cultures (A to C), and the pH and the number of lactic acid bacteria of the cultures (A to C) at the end of culture were measured. The results thereof are shown in Table 2. Next, 400 mL of liquid sugar syrup of glucose and sucrose, and 1.5 L of sterilized water were added to 600 mL of the culture. After homogenizing the mixture, the mixture was filled into 65 mL volume containers to produce lactic acid bacteria beverages (Products 1 to 3). The pH and the number of the lactic acid bacteria were measured immediately after the production of the beverages, and after 14 days preservation at 10° C. Regarding the lactic acid bacteria beverages after preservation, the amount of precipitation was confirmed visually, and the amount of precipitation and wheyoff (the amount of separated water) were measured. The results thereof are shown in Table 3.

Further, the amount of precipitation was evaluated visually, based on the following standards.

Evaluation Standard
1. Precipitation
++: Extremely large amount of precipitation
+: Precipitation confirmed
±: Extremely small amount of precipitation (no problem in a final product)
−: None

TABLE 2

|  |  | A | B | C |
|---|---|---|---|---|
| Medium Composition | Skim milk powder (Sample) | 16% | 16% | 16% |
|  | Phosphates* | 0.016% | 0.116% | 0.216% |
|  | Glucose | 3% | 3% | 3% |
| Free phosphoric acid concentration after the addition of phosphate compound based on the weight of the skim milk powder used for preparing the medium |  | 0.25% | 0.375% | 0.50% |
| pH after culture |  | 3.58 | 3.59 | 3.60 |
| Number of living bacteria at end of culture |  | $1.0 \times 10^9$ | $1.3 \times 10^9$ | $1.2 \times 10^9$ |

*A mixture of dipottasium hydrogen phosphate (50%) and potassium dihydrogen phosphate (50%)

TABLE 3

|  |  | Product 1 | Product 2 | Product 3 |
|---|---|---|---|---|
| Lactic acid bacteria culture |  | A | B | C |
| Immediately after production of product | pH | 3.78 | 3.78 | 3.79 |
|  | Number of living bacteria | $2.0 \times 10^8$ | $2.4 \times 10^8$ | $2.5 \times 10^8$ |
| After 14 day preservation at 10° C. | pH | 3.56 | 3.57 | 3.58 |
|  | Number of living bacteria | $1.2 \times 10^8$ | $1.3 \times 10^8$ | $1.2 \times 10^8$ |
|  | Precipitation (visually) | ± | ± | ± |
|  | Amount of precipitation* | 0.94% | 0.95% | 1.03% |
|  | Wheyoff | 6 mm | 6 mm | 6 mm |

Note)
The ratio of the amount of precipitation to the amount of a filled liquid was calculated by the following formula: D − C/A − C
D; The weight of the container and precipitation (The weight of the container with precipitation measured after the content in the container was gently discarded, and the container was left upside down for one minute.)
C; The weight of the container
A; The weight of the container and the filled liquid D; The weight of the container and precipitation
(The weight of the container with precipitation measured after the content in the container was gently discarded, and the container was left upside down for one minute.)
C; The weight of the container
A; The weight of the container and the filled liquid As Table 3 shows, the number of lactic acid bacteria in the obtained lactic acid beverage comprising lactic acid bacteria can be stably maintained by adding phosphates in a case where a milk ingredient having a free phosphoric acid concentration of less than 0.25% is used as a material.

In addition, the obtained lactic acid beverage had excellent flavor. No precipitation and separation was confirmed in the beverage after preservation thereof, and the beverage was excellent in product stability.

The invention claimed is:

1. A method of making a lactic acid bacteria beverage by fermenting lactic acid bacteria comprising the steps of:

providing a medium comprising a skim milk powder, the skim milk powder having a free phosphoric acid concentration of less than 0.25 wt % based on the weight of the skim milk powder and wherein a protein content per solid nonfat milk component (SNF) of the milk ingredient is less than 35 wt %;

selecting a phosphate compound for addition to said medium;

determining a free phosphoric acid concentration after the addition of the phosphate compound based on the weight of the skim milk powder, wherein the free phosphoric acid concentration is between about 0.25 wt % and about 0.5 wt % based on the weight of the skim milk powder;

determining an amount of the phosphate compound by calculation using the formula $$\frac{\left(\begin{array}{c}\text{free phosphoric acid}\\\text{concentration after}\\\text{the addition of}\\\text{phosphate}\\\text{compound based on}\\\text{the weight of the}\\\text{skim milk powder}\end{array} - \begin{array}{c}\text{free phosphoric}\\\text{acid concentration}\\\text{in skim milk}\\\text{powder used for}\\\text{preparing the}\\\text{medium}\end{array}\right) \times \left(\begin{array}{c}\text{the skim}\\\text{milk powder}\\\text{concentration}\\\text{in the}\\\text{medium}\end{array}\right) \times \left(\begin{array}{c}\text{molecular}\\\text{weight of the}\\\text{phosphate}\\\text{compound}\end{array}\right)}{100 \times (\text{molecular weight of phosphorus})}$$

wherein the skim milk powder concentration in the medium is between 5 wt % and 30 wt %;

adding the phosphate compound in the amount determined as above to the medium; and inoculating lactic acid bacteria to the medium, wherein the lactic acid bacteria is *Lactobacillus casei*, and wherein a pH of the medium subsequent to adding the phosphate compound is about 3.6.

2. The method of making a lactic acid bacteria beverage according to claim 1, wherein the phosphate compound is water-soluble.

3. A fermented milk product prepared by the method of making a lactic acid bacteria according to claim 1.

4. A lactic acid bacteria beverage prepared by the method of making a lactic acid bacteria according to claim 1.

5. The method of making a lactic acid bacteria beverage according to claim 1, further comprising:

mixing the medium with at least one of a thickener, an emulsifier, a vitamin agent, a syrup solution, a flavoring agent, a sugar, and combinations thereof to form a beverage; and storing the beverage at 10° C. for at least 7 days as a stable lactic acid bacteria beverage.

6. The method of making a lactic acid bacteria beverage according to claim 5, wherein the beverage exhibits less than 2% precipitation during storage at 10° C. for at least 7 days.

\* \* \* \* \*